United States Patent [19]

Langner

[11] Patent Number: 5,281,122
[45] Date of Patent: Jan. 25, 1994

[54] VESSEL FOR DUPLICATING DENTAL MODELS

[76] Inventor: Jan Langner, Birkachstrasse 17/1, D-7070 Schwäbisch-Gmünd, Fed. Rep. of Germany

[21] Appl. No.: 874,186

[22] Filed: Apr. 24, 1992

[30] Foreign Application Priority Data

Apr. 24, 1991 [DE] Fed. Rep. of Germany ....... 4113363

[51] Int. Cl.$^5$ .................. B29C 33/12; A61C 13/14
[52] U.S. Cl. .................... 425/116; 425/120; 425/192 R; 425/DIG. 11; 249/54; 249/93; 249/95
[58] Field of Search .................. 425/2, 116, 120, 125, 425/127, 123, 192 R, DIG. 11; 249/95, 93, 54; 264/19, 17, 18, 222, 225, 16

[56] References Cited

U.S. PATENT DOCUMENTS

| | | | |
|---|---|---|---|
| 2,421,698 | 6/1947 | Hordes | 249/54 |
| 3,074,112 | 1/1963 | Bobrow | 249/54 |
| 3,137,894 | 6/1964 | Butler et al. | 249/54 |
| 4,695,254 | 9/1987 | Herrell | 249/54 |
| 4,904,348 | 2/1990 | Domes et al. | 249/54 |
| 5,066,213 | 11/1991 | Ferincz | 249/54 |
| 5,175,008 | 12/1992 | Ueno | 425/178 |

FOREIGN PATENT DOCUMENTS 3906062 8/1990 Fed. Rep. of Germany .

*Primary Examiner*—Jay H. Woo
*Assistant Examiner*—Khanh P. Nguyen
*Attorney, Agent, or Firm*—Anderson Kill Olick & Oshinsky

[57] ABSTRACT

A vessel for duplicating dental models has at least two mold halves which can be clamped together. The mold halves have elements for mutually centering and for securing the model to be duplicated, for example, a tooth stump or the like. The vessel further includes an intake funnel each for pouring in liquid silicone and refractory casting material. A foil insert is provided in the plane of separation of the two mold halves when the vessel is closed. The foil insert has a thickness which corresponds in size to the setting expansion of the refractory casting material. The model to be duplicated is located in the center axis of the vessel and extends approximately by half its length through the foil insert and is held in position by the foil insert.

11 Claims, 2 Drawing Sheets

VESSEL FOR DUPLICATING DENTAL MODELS

BACKGROUND OF THE INVENTION

1. Field of the Invention

The present invention relates to a vessel for duplicating dental models. The vessel includes at least two mold halves which can be clamped together. The mold halves have elements for mutual centering and elements for securing the model to be duplicated, for example, a tooth stump or the like. The vessel further includes intake funnels each for pouring in liquid silicone and refractory casting material.

2. Description of the Related Art

Vessels or arrangements of the above-described type are known, for example, from German Offenlegungsschrift 39 06 062 and from German Utility Models 83 13 606 and 89 12 708. The technological background and the particular problems occurring in vessels or arrangements of this type are discussed in detail in these documents.

The document mentioned last, i.e., German Utility Model 89 12 708 (Kiefer) predominantly discusses the special peculiarities of the so-called setting expansion of the embedding material and proposes a precautionary measure to be carried out on the respective model for a subsequent compensation.

SUMMARY OF THE INVENTION

It is the object of the present invention to eliminate the disadvantages of the known systems. In addition, a vessel for duplicating dental models is to be provided which is substantially simpler to use and whose manipulation is improved over the known systems.

In accordance with the present invention, a foil insert is provided in the region of the plane of separation of the two mold halves when the vessel is closed. The foil insert has a thickness which corresponds in size to the setting expansion of the respective embedding material. The model to be duplicated is located preferably in the region of the center axis of the vessel and extends approximately by half its length through the foil insert and is held in position by the foil insert.

The various features of novelty which characterize the invention are pointed out with particularity in the claims annexed to and forming a part of this disclosure. For a better understanding of the invention, its operating advantages and specific objects attained by its use, reference should be had to the drawing and descriptive matter in which there is illustrated and described a preferred embodiment of the invention.

DESCRIPTION OF THE PREFERRED EMBODIMENT

Figure 1:
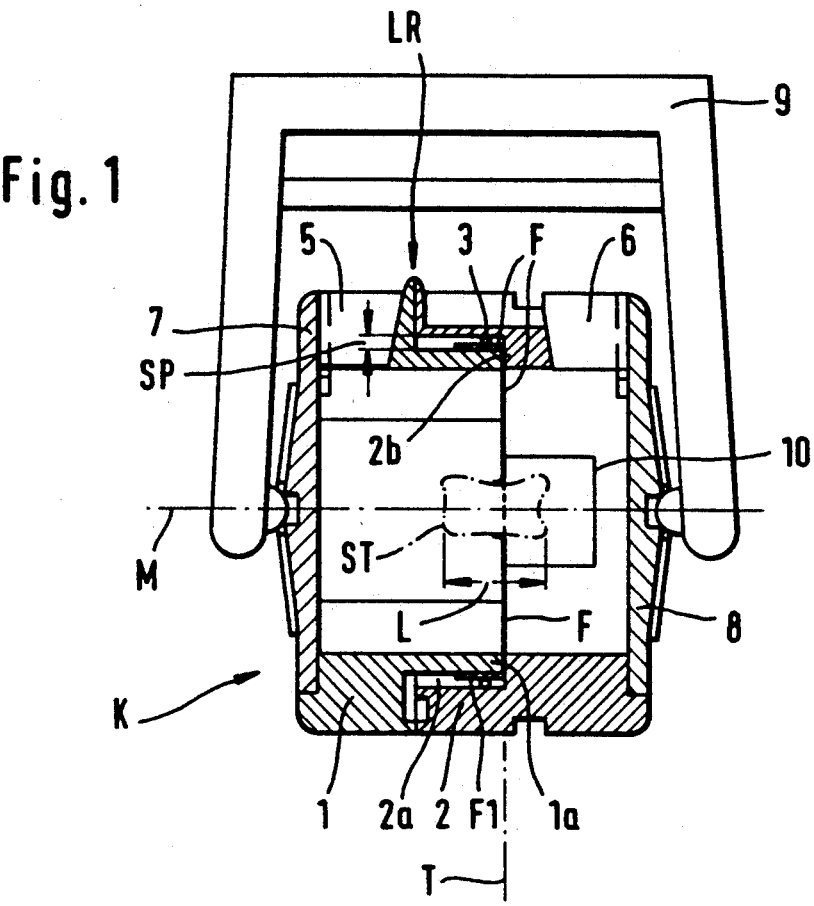
FIG. 1 is a longitudinal sectional view of the vessel for duplicating dental models according to the present invention.
Figure 2:
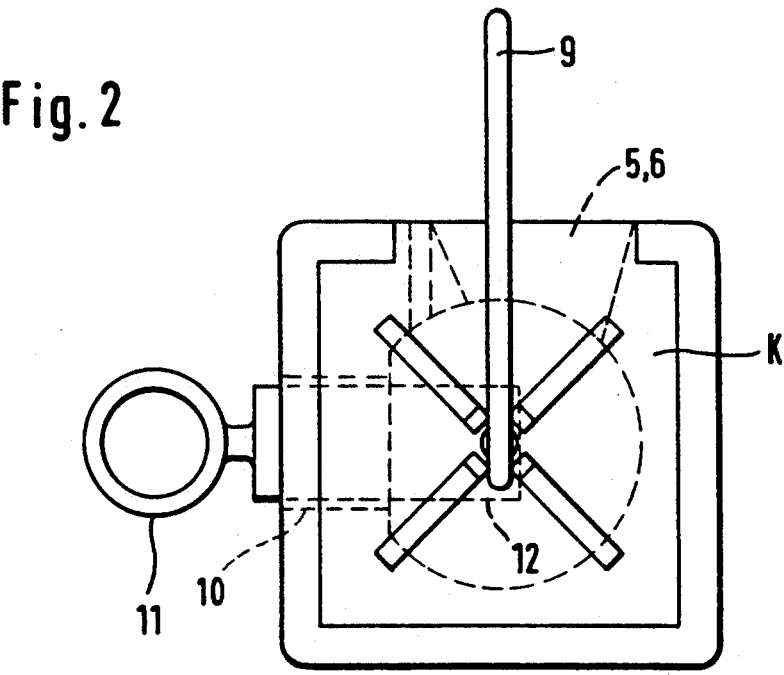
FIG. 2 is a side view of the vessel of FIG. 1.

FIGS. 1 and 2 of the drawing show the vessel K according to the present invention in the assembled state.

Figure 3:
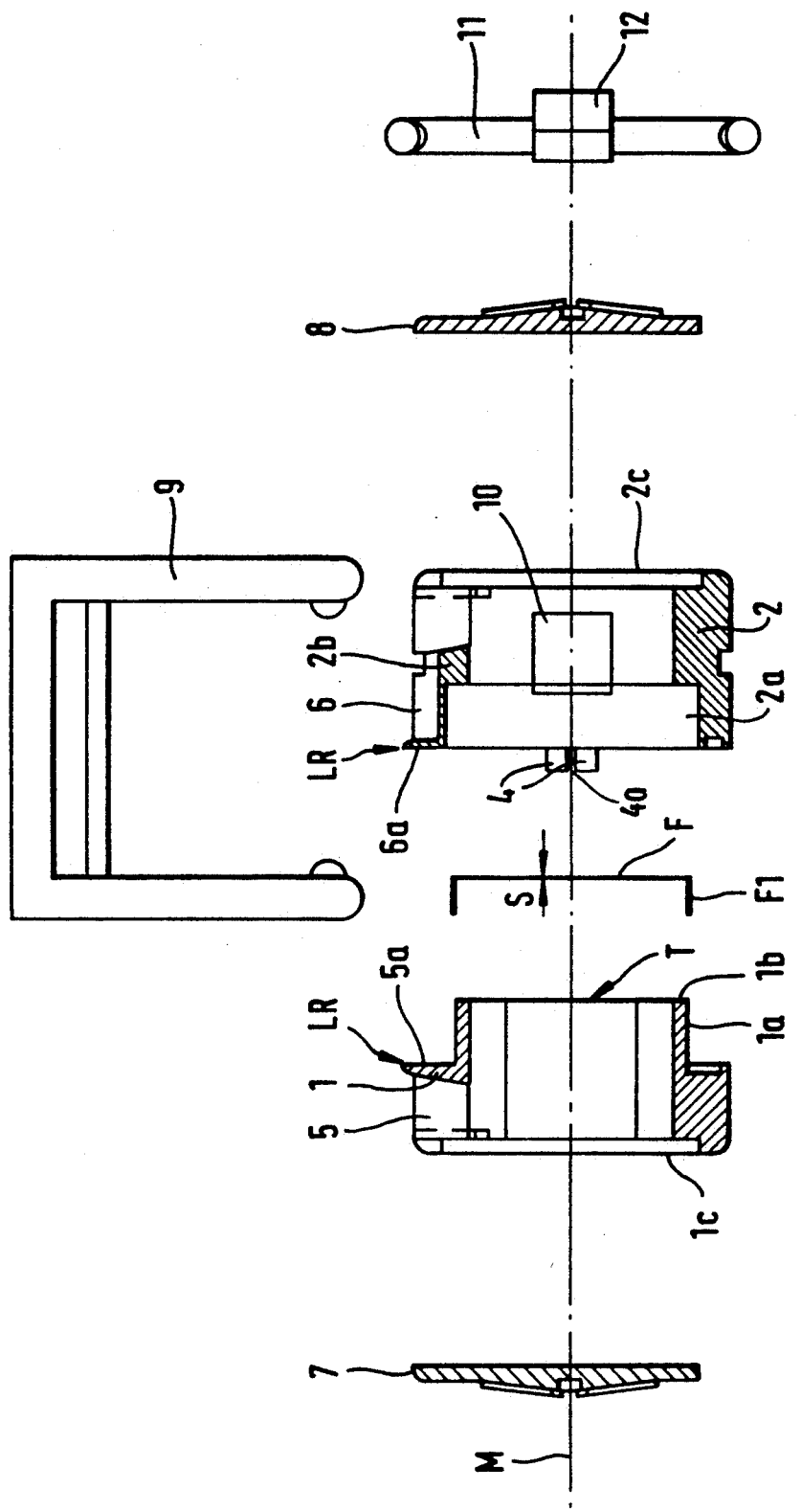
FIG. 3 is an exploded view showing the individual components of the vessel of FIG. 1.

FIG. 3 of the drawing shows the general configuration and the relative positions of operation of the individual vessel components.

Among the significant features of the vessel according to the present invention is a foil insert F located, when the vessel K is closed or assembled as shown in FIGS. 1 and 2, in the plane of separation T of the two mold halves 1 and 2. The foil insert F has a thickness S which corresponds to the magnitude of the setting expansion of the respective embedding material. The model to be duplicated, for example a tooth stump ST, is located preferably in the region of the center axis M of the vessel K and extends by approximately half its length L through the foil insert F and is held in position by the foil insert F because the material of the foil insert elastically contacts the outer wall of the tooth stump ST to be duplicated. The vessel K is dimensioned in such a way that, after the foil which does not adhere to the silicone and which supports the model has been taken out, the vessel K further closes by the thickness S of the foil, so that the setting expansion of the refractory material which has been filled into the vessel is compensated.

Another significant advantage of the present invention is to be seen in the fact that, when plaster models ST are transferred to refractory material which, as is well known, is required for the manufacture of ceramic inlays or veneers, not only the respective crown or the respective tooth stump itself is exactly duplicated, but the fastenings in the model, i.e., the bores for the so-called model pins, are also exactly duplicated.

In accordance with another structural feature of the present invention, one of the mold halves 1 of the vessel K has in the area of the plane of separation T a flange-type neck 1a, and the other mold 2 has a corresponding recess 2a with a stop shoulder 2b which limits the depth of insertion of the neck 1a. The foil insert F is clamped between the stop shoulder 2b and an end face 1b of the neck 1a. In the alternative, the foil insert F may be placed with its side or edges $F_1$ over the outer side of the neck 1a or may be tightly stretched over the neck 1a and held with a clamping ring 3. It is an operational advantage if the neck 1a and the recess 2a, which have a circular cross-section, are located with a play SP relative to each other in the radial direction and are held in a predetermined position relative to each other by means of centering elements 4 which are provided on the mold half 2 and define a gap 4a therebetween for receiving a rib (not shown) provided on the mold half 1.

In accordance with the another feature of the vessel according to the present invention, each of the mold halves 1 and 2 has on the same side a separate intake funnel 5 and 6 respectively whose adjacent walls 5a and 6a are located immediately next to each other. By constructing the end faces of the adjacent walls 5a and 6a as raised webs or as similar flow-dividing guide elements LR for the liquid silicone material, which abut each other in the assembled condition of the mold, as shown in FIG. 1, it is possible to simultaneously cast in both mold halves in one sequence, after the end faces 1c and 2c of the two mold halves 1 and 2 have been closed by means of covers 7 and 8 which are loosely held in place by means of a clamping stirrup 9 or the like. As shown in FIG. 3, there also may be provided a separate intake funnel 10 for the refractory material and a closing slide member 12 for closing the intake funnel 10. The slide member 12 is provided also with a ring member 11, which serves as a handle.

While a specific embodiment of the invention has been shown and described in detail to illustrate the application of the inventive principles, it will be understood that the invention may be embodied otherwise without departing from such principles.

I claim:

1. A vessel for duplicating dental models, the vessel comprising at least two mold halves, means for clamping the mold halves together, means for mutually centering the mold halves, each mold half having an intake funnel for receiving liquid silicone and refractory casting material, the two mold halves defining a plane of separation when the vessel is closed, a foil insert provided in the plane of separation, the foil insert having a thickness which corresponds in size to a setting expansion of the refractory casting material, the vessel having a center axis, the model to be duplicated being located essentially along the center axis of the vessel, the foil insert having an opening, the model having a length, the model extending by approximately half its length through the opening of the foil insert, whereby the model is held in position by the foil insert.

2. The vessel according to claim 1, wherein one of the mold halves has in the plane of separation a flange-like neck, the neck having an end face, the other of the mold halves having a recess which corresponds to the neck, the recess having a stop shoulder for limiting the depth of insertion of the neck, the foil insert being clamped between the stop shoulder and the end face of the neck.

3. The vessel according to claim 2, wherein the foil insert has an outer edge and side edges, the side edges extending over and being tightly tensioned on an outer side of the neck, the vessel further comprising a clamping ring for holding the outer edge of the foil insert.

4. The vessel according to claim 2, wherein the neck and the recess have a circular cross-section, wherein the neck and the recess are placed relative to each other with play in radial direction, and wherein the neck and the recess are held in engagement by the centering means.

5. The vessel according to claim 1, wherein the two intake funnels for the silicone are arranged separately and have limiting walls which are arranged immediately adjacent each other.

6. The vessel according to claim 5, wherein the adjacent limiting walls have end faces, the end faces forming together a raised web defining a flow-dividing guide for the liquid silicone.

7. The vessel according to claim 1, wherein the two mold halves have outer end faces, loosely mounted covers being provided for closing the outer end faces, the covers being held in position by the clamping means.

8. A vessel for duplicating dental models, the vessel comprising:
   at least two mold halves defining together a separation plane in a closed condition of the vessel and having each an intake funnel for receiving liquid silicone and a refractory casting material;
   means for centering the two mold halves in a closed condition of the vessel;
   means for clamping the two mold halves in the closed condition of the vessel together; and
   a foil insert provided in the separation plane for supporting a model to be duplicated in a predetermined position of the model in the vessel,
   wherein the foil insert has an opening for receiving the model to be duplicated, the opening having an axis which, in a mounted condition of said foil insert in said vessel, substantially coincides with a central axis of said vessel so that the model is located substantially along the center axis of the vessel, the model extending by approximately half of a length thereof through the foil insert opening, and wherein the foil insert has a thickness, which corresponds in size to a setting expansion of the refractory casting material, whereby the setting expansion of the refractory casting material that fills a cavity, which is formed by the model removable together with the foil insert before filling of the cavity, to duplicate the model, is compensated.

9. The vessel according to claim 8, wherein the intake funnels of the two mold halves have limiting walls which are arranged immediately adjacent each other in the closed condition of the mold.

10. The vessel according to claim 9, wherein the adjacent limiting walls have respective end faces which form a raised web defining a flow-dividing guide for dividing a flow of the liquid silicone into two flows directed to the two mold halves, respectively.

11. The vessel according to claim 8, further comprising a separate intake funnel for the refractory material for directing the refractory material into the cavity for duplicating the model, and a slide member for closing the separate intake funnel.

* * * * *